United States Patent [19]

Barnea et al.

[11] Patent Number: 4,567,896
[45] Date of Patent: Feb. 4, 1986

[54] METHOD AND APPARATUS FOR CALIBRATING A BIOPSY ATTACHMENT FOR ULTRASONIC IMAGING APPARATUS

[75] Inventors: Daniel Barnea; Moshe Epstein, both of Brookline, Mass.

[73] Assignee: Elscint, Inc., Boston, Mass.

[21] Appl. No.: 572,441

[22] Filed: Jan. 20, 1984

[51] Int. Cl.⁴ ............................................. A61B 10/00
[52] U.S. Cl. ...................................... 128/660; 73/1 R
[58] Field of Search ................................. 128/660–663, 128/24 A; 73/1 R, 1 DV, 597

[56] References Cited

U.S. PATENT DOCUMENTS

| | | | |
|---|---|---|---|
| 3,023,611 | 3/1962 | Howry | 128/660 X |
| 4,108,165 | 8/1978 | Kopp et al. | 128/660 |
| 4,151,834 | 5/1979 | Sato et al. | 128/660 |
| 4,170,891 | 10/1979 | Elsner | 73/1 R |
| 4,346,717 | 8/1982 | Haerten | 128/660 |
| 4,363,326 | 12/1982 | Kopel | 128/24 A X |
| 4,373,532 | 2/1983 | Hill et al. | 128/660 |
| 4,401,124 | 8/1983 | Guess et al. | 128/660 |
| 4,402,324 | 9/1983 | Lindgren et al. | 128/660 |
| 4,407,294 | 10/1983 | Vilkomerson | 128/660 |
| 4,463,592 | 7/1984 | Flax et al. | 734/1 DV |
| 4,476,549 | 10/1984 | Dragonette et al. | 73/1 DV |

OTHER PUBLICATIONS

Baksheev, V. et al., "Eqpmt. for Measurement of UTS Transducers", Meas. Tech. (USA) vol. 23, No. 5 (May 1980) (publ. Oct. 1980).

Hall, A. J. et al., "A Method of Calibrating Contact B-Scanners", UTS, Nov. 1976 vol. 16, No. 6, Nov. 1978.

"Ultrasound Phantoms" (sales brochure) ATS Laboratories, P.O. Box 792, South Norwalk, Conn. 06856.

Primary Examiner—Kyle L. Howell
Assistant Examiner—Francis J. Jaworski
Attorney, Agent, or Firm—Sandler & Greenblum

[57] ABSTRACT

A sector-scan ultrasonic imaging apparatus includes a biopsy attachment mounted on the housing of the imaging apparatus for positioning a biopsy needle relative to the ultrasonic scan head of the imaging apparatus. An image display device displays both an image of the region scanned by the scan head and a predetermined, superimposed electronic representation of the position of the biopsy needle-line relative to the probe scan head. The biopsy needle-line is calibrated with a scan head coordinate system which defines a sector sweep of the scan head by determining the coordinates of the needle-line in the scan head coordinate system independently of determining the particular spatial relationship of the needle-line in operative position relative to the scan head. A calibration member adapted to be mounted on the biopsy attachment includes at least two ultrasonic reflection regions which are scanned by the scan head during the calibration mode and displayed on an image display device. The display of these at least two reflection regions enables the needle-line coordinates to be determined using the predetermined geometric relationship of the calibration member with respect to the imaging apparatus housing. Alternatively, the calibration member can include a single ultrasonic reflection region, and an angular detector can be used to determine the angular orientation of the calibration member relative to the probe scan head, to enable the needle-line coordinates to be determined.

25 Claims, 7 Drawing Figures

METHOD AND APPARATUS FOR CALIBRATING A BIOPSY ATTACHMENT FOR ULTRASONIC IMAGING APPARATUS

FIELD OF THE INVENTION

The present invention relates to a method of and apparatus for calibrating a biopsy attachment for ultrasonic imaging apparatus.

BACKGROUND OF THE INVENTION

In general, ultra-sound imaging techniques use a pulse-echo method wherein short pulses of ultrasonic energy generated by a piezoelectric transducer are focused to a narrow beam and transmitted through a suitable conducting medium, usually water, into the body of a patient. A portion of the ultrasonic energy is reflected back toward the transducer at tissue interfaces between various different bodily structures due to mechanical impedance discontinuities at the interfaces. The transducer receives the reflected energy and converts it into electrical signals. The time of arrival of the returning reflected signals indicates the relative positions within the body of the interfaces. In other words, the timed spacing between the reflected signals or echoes is proportional to the physical spacing of the respective reflecting interfaces within the body; and the amplitude of the echo is a function of the characteristics of the structures forming the interface.

The image-representing electrical signals corresponding to the characteristics of the reflected mechanical energy are then displayed, generally, on a "B-scan" display. Such a display is comparable to a conventional television display. In such a system, the reflected echo signals modulate the brightness of the display at each point scanned. Strongly reflecting internal structures, such as hardened artery walls, appear brighter on the display than weakly reflecting structures. This gray scale produces a useful diagnostic tool.

A plurality of scan lines can be produced by scanning the ultrasonic beam produced by the transducer at a predetermined rate and in a predetermined direction across the surface of the patient. The plurality of scan lines so produced can be used to yield a sector-shaped display of a cross-sectional picture in the plane of the scan produced by the reflector-scanner, which scans mechanically over a desired angle.

A typical sector scan probe is illustrated in U.S. Pat. No. 4,151,834, the disclosure of which is hereby incorporated by reference. This patent shows a housing containing a DC servomotor that drives a mechanism for oscillating a transducer crystal. The transducer is periodically pulsed with electrical signals causing an ultrasonic beam to be emitted periodically as the transducer oscillates between its angular limits. The rate at which the transducer is pulsed is many times greater than the rate of angular movement of the transducer; for this reason, the beam is said to scan a sector.

Some medical procedures are facilitated when a biopsy needle is used in conjunction with the ultrasonic probe, and for this reason, spatial ultrasonic probes have been developed to achieve this purpose. U.S. Pat. No. 4,108,165 discloses an ultrasonic probe having an annular transducer periodically driven by an electronic circuit for producing ultrasonic beams which can be directed into the body of a patient under examination. In the device disclosed in this patent, no scanning of the beam is provided, and the transducer is mounted in a cylindrical housing having an axial bore concentric with the annular transducer. The biopsy needle is concentrically located within the probe to align the biopsy needle with a biopsy target in the body under examination.

In general, high accuracy biopsy can be accomplished using a biopsy attachment mounted on a scanning ultrasound probe where the attachment is of the type which includes a needle guide for orienting the biopsy needle accurately toward a biopsy target according to the following procedure. First, the patient is ultrasonically scanned and the biopsy target is located on the display screen. The display also includes a predetermined, superimposed electronic representation of the position of the needle-line relative to the probe scan head, where the needle-line is defined as the line along which the biopsy needle would travel while being inserted through the needle-guide. To align the needle-line with the biopsy target, the ultrasound probe is moved relative to the body under examination until the displayed needle-line passes through the image of the biopsy target on the display screen. In order to determine the distance to the biopsy target, a movable cursor associated with the display device can be moved to the displayed biopsy target. By calibrating the position of the cursor, the distance to the target can be determined.

The above-described technique is generally illustrated by U.S. Pat. No. 4,346,717 which discloses an ultrasonic probe designed to facilitate the use of a biopsy needle. This system produces and electronically superimposes on a display screen image of the body under examination a guide image beam which corresponds to the orientation of a needle guide for a puncturing biopsy needle. The coordinates of the guide image beam on the display screen are calculated by using the value of the angle $\theta$ which defines the angular relationship between the needle guide and the ultrasonic probe. An angle detector is employed for precisely detecting the angle of the guide sleeve relative to the ultrasonic probe. If the guide sleeve is arranged at a fixed angle $\theta$, aiming of the puncturing needle relative to the target area is accomplished by spatially displacing the ultrasonic probe on the surface of the body, and adjusting the attitude of the probe, until the guide beam superimposed on the displayed image passes through the biopsy target area to be punctured. If the position of the guide sleeve is adjustable with respect to the probe, adjusting the guide sleeve causes the guide image beam to likewise be adjusted via positioning signals which are obtained as a function of an angle-adjusting element which functions to reposition the guide sleeve; thus, the guide sleeve is moved until the guide image beam passes through the biopsy target shown on the display screen.

Both the above-described general ultrasound biopsy procedure as well as that disclosed in U.S. Pat. No. 4,346,717 require the generation of a guide image beam which electronically represents the biopsy needle-line on the display screen and which is superimposed on the displayed ultrasound image of the scanned body section which includes the biopsy target. In heretofore known systems, in order to show the needle-line on the display, the system must determine, for example, by direct measurement or precision manufacturing, the geometry of the needle guide, and hence that of the needle-line, in the scan head coordinate system which defines the sector sweep of the ultrasound scanning head associated with the ultrasound imaging apparatus; this coordinate system can conveniently be expressed in polar coordinates employing the scan angle and the range r.

However, in most ultrasound probe systems having biopsy attachments, although the spatial relationship between the needle guide and the housing is known because the biopsy attachment is mounted on the probe housing, the spatial relationship between the scan head and the probe housing is generally not precisely defined because the imaging system does not require it. As a result, the geometry of the needle guide in the scan head coordinate system is also not precisely defined. The system disclosed in U.S. Pat. No. 4,346,717 solves this problem by providing a needle guide attachment which is, unlike most ultrasound probe systems, precisely disposed at a known angle $\theta$ with respect to the ultrasound scan head. Disadvantageously, this requires a high degree of manufacturing precision with respect to the tolerances between the biopsy attachment, the probe housing, and the scan head, resulting in increased costs. It also requires calibration at the factory. Alternatively, as noted above, the system disclosed in U.S. Pat. No. 4,346,717 employs an angle detector to determine this angle, also resulting in additional components and increased costs.

It would be advantageous to eliminate the necessity of determining the particular spatial relationship between the scan head and the needle-line in order to calibrate the biopsy attachment with the scan head coodinate system so that the needle-line can be superimposed on the display screen. It is, therefore, an object of the present invention to provide an ultrasonic imaging apparatus biopsy attachment calibration method and apparatus which provides this capability and which overcomes the above-described deficiencies in the prior art.

SUMMARY OF THE INVENTION

The present invention is particularly suitable to what is termed multiprocessor based realtime ultrasonic sector scanners, hereinafter termed ultrasonic imaging apparatus of the type described. An example of such apparatus is the Dynex line of ultrasonic imaging apparatus currently being marketed by Elscint, Inc., 930 Commonwealth Avenue, Boston, MA 02215.

Apparatus of the type described comprises an ultrasonic probe having a housing into which a scan head is mounted for oscillatory motion to define a sector-shaped scanning region (typically from 30° to 60°), and electronic processing and display circuitry for realtime processing and display of the signals developed by the probe. Such circuitry comprises memory means for storing data representative of an image of the region scanned by the head, and an image display means responsive to the memory means for displaying a realtime image of the region scanned by the scan head. The display means of the apparatus includes a processor for creating a cursor in the displayed image which is manually positionable by an operator to various locations in the displayed image, and for computing the coordinates of the location of the cursor in the scan head coordinate system.

The housing of the probe is provided with a biopsy attachment for positioning a biopsy needle so that its needle-line has a particular spatial relationship with the scan head when the needle is mounted in operative position on the housing. The present invention provides for an improved method for aligning the needle-line with a biopsy target by creating a computer generated pseudo needle-line which is superimposed on the realtime image contained in the memory means. Such method is based on a calibration procedure that does not require independent determination of the particular spatial relationship of the actual needle line of a biopsy needle when the latter is in its operative position. In other words, no knowledge is needed of the relationship between the angle of the biopsy needle and the centerline of the scan head, for example, and the position of the biopsy attachment on the housing relative to the scan head, etc., because of the calibration procedure of the present invention. Such procedure includes mounting a calibration member on the biopsy attachment, immersing the member in a suitable fluid, e.g., water, operating the imaging apparatus to scan the calibration member, and storing the data so obtained in the memory means. The calibration member may have two spaced sonic reflection regions, preferably in the form of substantially spherical reflection members such that a line connecting the two regions is congruent to the biopsy needle-line when the biopsy needle is in its operative position.

The two reflection regions appear as visually distinguishable bright spots in the display generated during the calibration procedure; and an imaginary line passing through the two spots defines the biopsy needle line in the display. The coordinates of the line passing through the bright spots are computer generated by sequentially moving the cursor into overlying relationship with each of the bright spots to allow the computer to acquire the individual coordinates of the spots in the scan head coordinate system. From this information, the computer then generates and stores the coordinates of the line passing through the two bright spots.

Alternatively, only one reflection member can be used instead of two; but in this case, the computer must be furnished with the coordinates of the single bright spot, obtained by manually positioning the cursor on the spot, and with the angular relationship of the biopsy needle-line with respect to the scan head. With these data, the coordinates of the pseudo needle-line can be computed and stored.

By following the above described calibration procedure, the memory means will contain data which, when the contents of the memory means is displayed, will produce a reference line of predetermined, visually distinguishable, intensity representing the calibration member. When the apparatus is used in a clinical imaging situation, the reference line will appear in the display superimposed on the clinical image. The reference line coincides with the biopsy needle-line when the needle is mounted in operative position even though the needle itself will not be visible in such image.

In operation in a clinical imaging situation, the medical technician would adjust the ultrasonic imaging apparatus (without the biopsy needle mounted in operative position) relative to the patient until the reference line in the image passes through the biopsy target region in the image. In this position of the apparatus, the technician is assured that insertion of a biopsy needle into the biopsy attachment on the housing of the apparatus will result in the penetration of the needle into the target region.

The invention is also applicable to ultrasonic imaging apparatus of the type described wherein the probe is provided with a biopsy attachment that is adjustable to more than one position such that the angle made by the biopsy needle relative to the centerline of the probe head is selectively adjustable. The calibration procedure described above is carried out for each position of the biopsy attachment; and the computer stores the coordinates of the pseudo needle-lines such that they can be retrieved from memory in accordance with the particular adjustment of the the biopsy attachment in current use. The adjustment can be sensed by a transducer which will automatically select the appropriate coordinates to be used in a display; or, direct operator input can be used to specify the adjustment and effect selection of the appropriate set of coordinates.

BRIEF DESCRIPTION OF THE DRAWINGS

Embodiments of the invention are shown in the accompanying drawings, wherein.

DETAILED DESCRIPTION OF THE INVENTION

Figure 1:
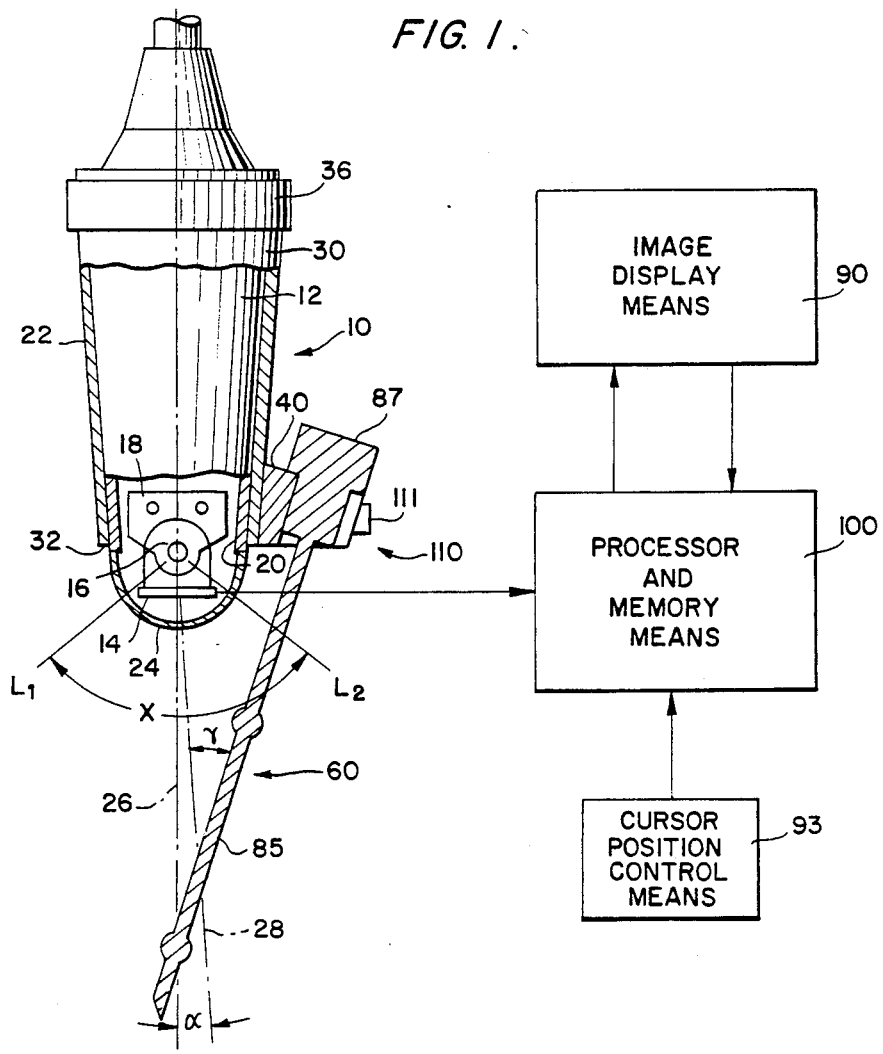
FIG. 1 is a vertical cross-sectional view through an ultrasonic imaging apparatus which includes a biopsy attachment having a mounted calibration member according to the present invention.

Referring now to FIG. 1, reference numeral 10 designates a biopsy attachment according to the present invention attached to sector scan ultrasonic imaging apparatus 12. The details of imaging apparatus 12 are of no concern in the present application, and only transducer scan head 14 is shown in detail. Transducer scan head 14 is mounted on bearing 16 carried by a support 18 rigidly attached to imaging apparatus 12 adjacent open end 20 of housing 22 containing the imaging apparatus. Support 18 carries a position sensor (not shown). By a suitable mechanism, such as a servo system (not shown), transducer scan head 14 is oscillated or scanned between two limits designated L1 and L2 in FIG. 1 which define a sector sweep.

Open end 20 of housing 22 is closed by a plastic sheath 24, which is transparent to sonic radiation produced by transducer scan head 14 or reflected back to transducer 14 from an object producing an echo. Phantom line 26 defines the geometric center-line of the transducer; and the mechanism (not shown) housed within housing 22 causes the transducer to oscillate about bearing axis 26 producing a beam whose azimuth angle changes from the angular position shown by line L1 to the angular position shown by line L2. This movement occurs at around 30-70 scans per second, while the transducer is pulsed at a rate many times faster. As a result, many ultrasonic beams will be located within the sector sweep defined by the lines L1 and L2.

When the scan head is commanded by the servo system to go to its zero position, the actual center line of the beam, as designated by broken line 28, is displaced from the geometric zero position by the angle $\alpha$. This angle is usually quite small and provides an error whose magnitude depends on the precision with which the electronics driving the transducer and the transducer mounting itself are fashioned. As discussed previously, a sector scan probe can have a DC motor which is servo-controlled and a support 18 to which is mounted a position sensor (not shown) which establishes the angle of the transducer and which feeds this information back to the motor for controlling its operation. By suitable calibration, the angle $\alpha$ can be made small.

Biopsy attachment 10 includes tubular housing 30 formed of relatively thin plastic material dimensioned to closely fit around imaging apparatus 12, as shown in FIG. 1. The operational free end 32 of tubular housing 30 is open permitting plastic sheath 24 to project therethrough. The opposite axial end of housing 30 is also open and is threaded. Because sector-shaped imaging apparatus are generally tapered, as indicated in FIG. 1, tubular housing 30 is held in place with imaging apparatus 12 via screw cap 36, which is releasably connected to tubular housing 30 via screw threads 34 (shown in FIG. 5). Thus, tightening of cap 36 draws housing 30 into close engagement with imaging apparatus 12. Also, a groove (not shown) between probe end cap 36 and housing 30 includes a rubber ring seated over a thin protective drape, such that biopsy attachment 10 is held in place by tightening cap 36. This tightening encloses the rubber ring between biopsy attachment housing 30, cap 36 and the aforementioned groove and provides a very firm grip over imaging apparatus 12.

Figure 5:
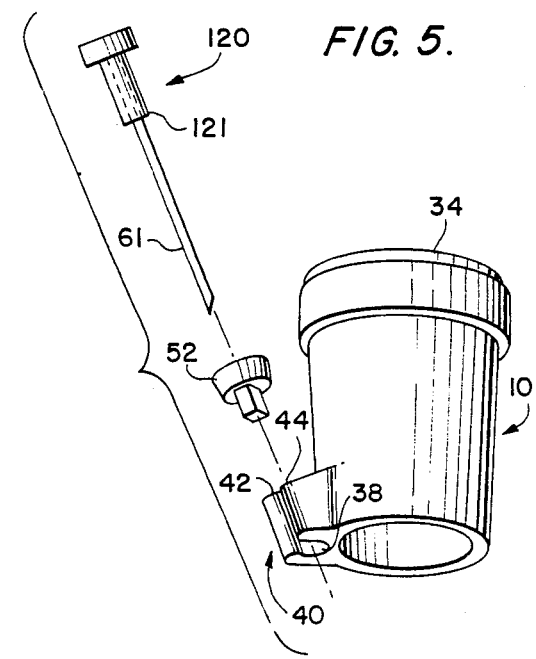
FIG. 5 is a perspective view of the biopsy attachment according to the present invention shown with its parts exploded, and illustrating stop means for stopping the insertion of a biopsy needle in a needle guide at a range corresponding to the position at which a biopsy target is located.

In addition to tubular housing 30, biopsy attachment 10 includes needle guide means 40 mounted on tubular probe housing 30 via tubular housing 30, for orienting a biopsy needle toward a biopsy target. Needle guide means 40 can be a bushing holder or lug, as illustrated in FIGS. 1 and 5, for receiving a bushing 87 of a calibration member 60 (FIG. 1) or a needle guide bushing 52 (FIG. 5) into which a biopsy needle 61 has been mounted, as disclosed in co-pending U.S. patent application Ser. No. 529,624, filed Sept. 6, 1983, the disclosure of which is hereby incorporated by reference.

According to the present invention, calibration member 60 is mounted on biopsy attachment 10 by means of needle guide means 40 which, in the embodiment shown in FIG. 5, preferably includes a bushing holder or lug 40 which includes spaced legs 42, 44, leading to recess 38.

Figure 2:
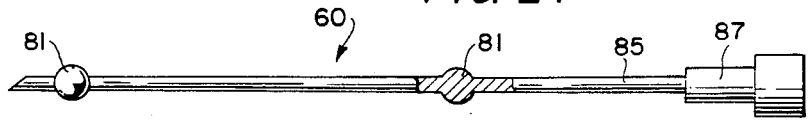
FIG. 2 illustrates a calibration member according to the present invention.

FIG. 2 illustrates calibration member 60 in an embodiment which includes a substantially straight rod 85 on which are mounted ultrasonic reflectors 81, which are preferably substantially spherical balls, and a bushing 87 preferably integral with or permanently affixed to one end of rod 85. Reflectors 81 can be integral with rod 85, or, alternatively, can be movably mounted thereon, e.g., they could be formed with a substantially central bore which frictionally engages rod 85. Rod 85 is preferably a small diameter rod or wire. Bushing 87 is adapted for mounting within needle guide means 40 of biopsy attachment 10. When calibration member 60 is mounted within guide means 40, reflection members 81 are disposed such that they lie within the region of the sector sweep of scan head 14, and thus, will reflect a transmitted ultrasound beam back to transducer 14 during a scanning operation. Accordingly, during a calibration scanning operation, the location of reflection members 81 will be displayed on image display means 90 associated with the ultrasonic imaging apparatus. Using this display, the coordinates of members 81 within a scan head coordinate system which is used to define a sector sweep of scan head 14 can be determined and stored in memory unit 100. These stored coordinates are then used to calculate the coordinates of the biopsy needle-line in this same coordinate system. These biopsy needle-line coordinates are then stored in memory unit 100 where they can be used to provide a predetermined, superimposed electronic representation of the entire biopsy needle-line on image display means 90.

Figure 4A:
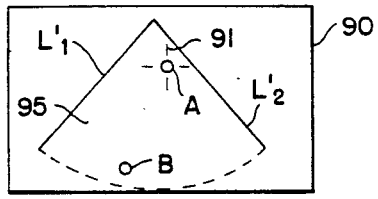
FIGS. 4a and 4b illustrate another step in a method according to the present invention of calibrating a biopsy attachment with a scan head coordinate system.
Figure 4B:
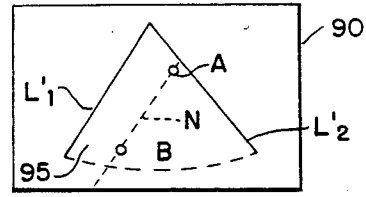
Figure 3:
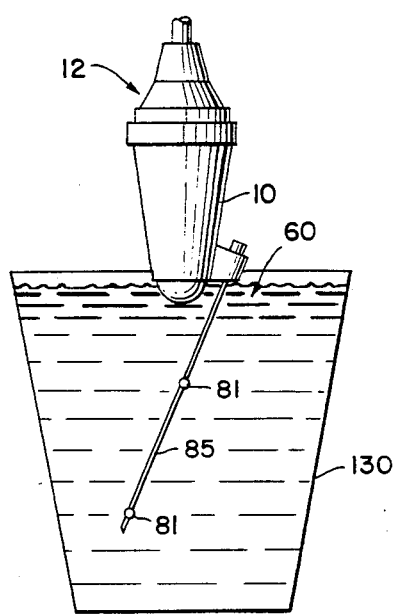
FIG. 3 illustrates a step in a method according to the present invention of calibrating a biopsy attachment with a scan head coordinate system.

One technique for determining the coordinates of reflection members 81 includes, as shown in FIGS. 3, 4a and 4b, positioning a movable cursor 91, shown as a "cross", displayed on sector-shaped display screen 95 associated with image display means 90 via cursor control means 93 which may be a joy stick or other positioning device. Cursor 91 is successively positioned at the displayed positions A and B of reflection members 81; these displayed positions are obtained after immersing calibration member 60 including reflection members 81 in a fluid held by a small tank 130 which may even be a styrofoam cup. The coordinates in the scan head coordinate system of cursor 91 at these points are then determined and stored in memory unit 100, for use in determining the coordinates of the biopsy needle-line. As before, the biopsy needle-line coordinates are stored, and subsequently used, as desired, to provide an electronic representation of the needle-line on the display device. Cursor control means 93 may be used to alter the position of cursor 91 by means of data signals provided by computer and memory unit 100 to image display means 90 in any suitable manner known in the art.

Adjustment means 110 shown in FIG. 1 provides for adjustment of the spatial relationship of needle guide means 40 relative to probe housing 22 and transducer scan head 14 such that the biopsy needle-line has a multiplicity of operative positions relative to scan head 14. At each setting of adjustment means 110, the biopsy needle-line has a particular spatial relationship in operative position relative to the scan head. For each such operative position, a separate calibration of the needle-line within the scan head coordinate system is necessary. Memory unit 100 is employed to store the biopsy needle-line coordinates for each operative position. The particular coordinates stored in memory unit 100 which are used to provide the superimposed needle-line display on image display means 90 will be determined by the setting of adjustment means 110. In FIG. 1, adjustment means 110 is shown in an embodiment which includes a plate 111 which is fixed to tubular housing 30 and onto which needle guide means 40 is movably mounted.

FIG. 5 illustrates stop means 120 for stopping the insertion of a biopsy needle 61 in needle guide means 40 at a range corresponding to the position at which a biopsy target is located. Stop means 120 in one embodiment can be a sleeve 121 having an adjustable length. The sleeve length corresponding to the desired range for the specific needle length can be selected or cut, and mounted on the biopsy needle. Alternatively, a conventional needle stop could be employed, e.g., a stop comprising a ring having a central bore which can be adjustably secured on the biopsy needle via a side screw which frictionally contacts the needle.

By the above method and apparatus, the coordinates of the biopsy needle-line in the scan head coordinate system are determined independently of determining the particular spatial relationship of the needle-line in a particular operative position relative to the scan head. Using the method and apparatus of the present invention, there is no need to determine the particular spatial relationship of the needle-line relative to the scan head when the needle is in operative position relative to the scan head. This provides a simpler, less expensive device than has been heretofore known, eliminating the need for providing high mechanical tolerances in manufacturing the ultrasonic probe housing, the transducer scan head and the biopsy attachment as a precondition to determining the needle-line coordinates in the scan head coordinate system for superimposing the needle-line on the probe display.

It should be noted that calibration member 60 is not limited to the particular structure shown in FIG. 2, but that alternatively rod 85 can be provided with many different shapes. Also, rod 85, bushing 87, and reflection members 81 can be formed as a single integral unit or as an assembly. Alternatively, members 81 can be movably mounted on rod 85, e.g., as discussed above. Moreover, reflection members 81 can be spherical in shape, or can have other alternative shapes, with the sole requirement being that members 81 must reflect the transmitted ultrasonic beam back to transducer 14. Thus, it can be seen that, as an additional alternative, reflection members 81 can be formed as "holes" in an ultrasound transparent material.

Preferably, when calibration member 60 is mounted in guide means 40, substantially straight calibration rod element 85 will be disposed along the line along which a biopsy needle would be disposed were the biopsy needle mounted on the biopsy attachment. This eliminates the need for additional computations which would otherwise be necessary, based on a known predetermined geometrical relationship between the orientation of rod 85 and probe housing 22, to obtain the coordinates of the biopsy needle-line in the scan head coordinate system once calibration member 60 has been scanned by the probe during the calibration mode. However, it should be noted that so long as the orientation of rod 85 bears a known geometrical relationship with respect to probe housing 22, and thus with respect to the biopsy needle-line, the desired coordinates of the needle-line in the scan head coordinate system can be obtained through easily derived mathematical methods. In other words, although calibration member 60 is preferably in the shape of a needle, i.e., small-diameter, substantially straight rod 85, member 60 need not be provided with this shape. Any calibration member which is affixed to probe housing 22 with a known, defined geometry and which has ultrasound reflection regions capable of reflecting a transmitted ultrasound beam back to the transducer and, as a result, capable of precisely geometrically defining the orientation of the biopsy needle guide hole, may be employed to provide a calibration member. Therefore, a "phantom" member 200 (FIG. 6) which has any desired arrangement of ultrasound reflection members, or regions 81, on which a geometrically defined structure will be placed or attached which enables the probe housing to be mounted or attached to "phantom" member 200 in a geometrically defined manner in order to provide a capability of determining the orientation of the needle-guide hole in the scan head coordinate system could be employed as a calibration member according to the present invention.

Figure 6:
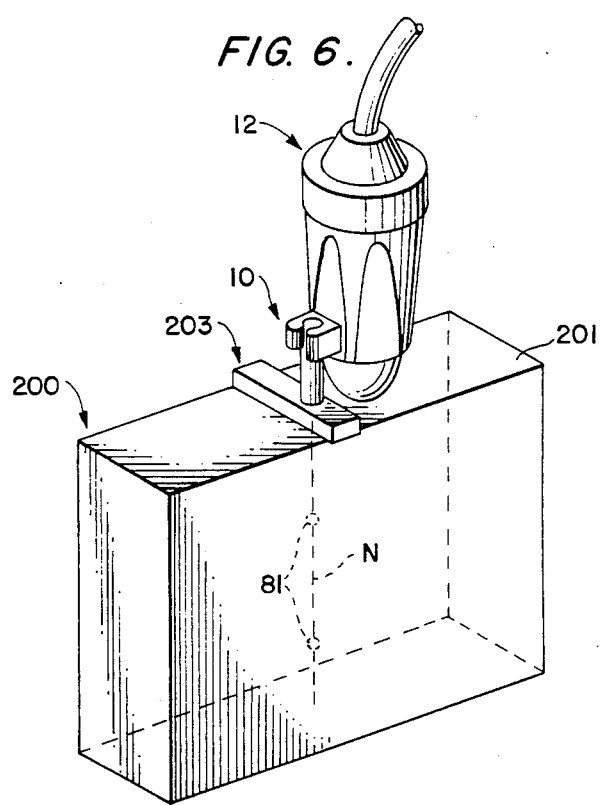
FIG. 6 illustrates a calibration member according to another embodiment of the present invention.

FIG. 6 discloses an alternative embodiment of the present invention which includes a calibration member 200 which includes second housing 201 and mounting means 203 for mounting imaging apparatus 12 and biopsy attachment 10 mounted thereon on second housing 201 in a predetermined geometrical relationship such that needle-line N of the biopsy needle is defined. At least one reflection region 81 is disposed in housing 201 on any convenient point on needle-line N, although a plurality of members or regions 81 could be employed if desired. Housing 201 can include a reservoir for holding fluid for use during calibration scanning by the scan head. Mounting means 203 can include means for mounting the imaging apparatus and the biopsy attachment mounted thereon in multiple discrete operative positions of the biopsy needle relative to the scan head mounted in the imaging apparatus housing. It should be noted that only one reflection region 81 is necessary to determine the needle-line coordinates in the scan head coordinate system where the angular orientation of needle-line N relative to the scan head of imaging apparatus 12 is known. This angular orientation can be determined via precisely manufacturing the various parts, or, alternatively, via angle measurement means which can be provided to measure this angular orientation. Thus, by determining the coordinates of a single reflection region 81, the coordinates of each other point along line N can also be determined from the predetermined angular orientation between needle-line N of calibration member 200, and the scan head. In other words, when the angular orientation of the needle-line N is determined, the set of possible orientations for needle-line N includes all parallel lines having this given angular orientation; from a mathematical perspective, it is clear that by locating one point along the actual line N, the coordinates of the entire line N can be determined.

Referring again to FIG. 1, calibration member 60 need only include at least one reflection member or region 81 to reflect back the transmitted ultrasound beam to the transducer in the case where angle measurement means 181 is provided to measure the angular orientation of rod 85 relative to probe housing 22, or alternatively, where this angular orientation is determined via other techniques, such as by precision manufacturing of biopsy attachment 10 mounted on probe housing 22, and calibration member 60 and the transducer scan head mounted in probe housing 22. As discussed above, one reflection member or region 81 in such case is sufficient because, by determining its coordinates, the coordinates of each other point along rod 85 are also known. Also as explained above, computer and memory means 100 is used to store data representing this measured or determined angular orientation and to calculate the coordinates of needle-line N for ultimate superimposed display on image display means 90. On the other hand, the needle-line coordinates can be determined totally independently of the predetermined geometric relationship between the needle-line and the scan head, (i.e., without determining the value of the angular orientation of the needle-line relative to the scan head and, further, without actually determining any other physical parameter relating to this geometric relationship, by using a calibration member which includes at least two reflection members or regions 81. In such case, during calibration scanning, the coordinates of at least two-positions on rod 85 must be determined in order to provide sufficient data for computer and memory means 100 to determine the orientation of the needle-line relative to the scan head coordinate system and to calculate the coordinates of the needle-line.

According to the present invention, the above-described calibration can be performed either by the manufacturer at the factory or by the user. The needle-line coordinates can be, for example, fed into the ultrasonic imaging apparatus system computer non-volatile memory. The user need only check the probe needle-line calibration occasionally, and update the computer memory if necessary.

From the foregoing description, one skilled in the art can easily ascertain the essential characteristics of the present invention and, without departing from the spirit and scope thereof, can make various changes and modifications of the invention to adapt it to various usages and conditions.

We claim:

1. A method for using an ultra-sonic imaging apparatus which includes a scan head mounted in a housing and operable to scan a sector defining a scan head coordinate system, memory means responsive to said scan head for storing images of a region scanned by said scan head, image display means for displaying said images stored in said memory means and for displaying a manually positionable cursor, and a biopsy attachment mounted on said housing for positioning a biopsy needle so that its needle-line lies within the region scanned by said scan head when the needle is in operative position on said housing, said method comprising the steps of mounting on said biopsy attachment a calibration member that simulates the needle-line of a biopsy needle for producing a display of said calibration member when said scan head is operated, determining coordinates of the calibration member in said scan head coordinate system, storing said coordinates of the calibration member in said memory means, calculating from said stored coordinates the coordinates of said needle-line in said scan head coordinate system, and storing said coordinates of said needle-line in said memory means.

2. The method as recited in claim 1, wherein said coordinates of the simulated needle-line in said scan head coordinate system are determined by displaying the display of said calibration member on said image display means, moving said cursor to at least two points on said display of said calibration member, determining the coordinates of said cursor at said at least two points in said scan head coordinate system, and storing said cursor coordinates in said memory means.

3. The method according to claim 2 wherein said calibration member includes at least two ultra-sonic reflection members and further comprising the steps of determining the coordinates of said two reflection members in said scan head coordinate system, storing said coordinates of said two reflection members in said memory means, calculating from said stored coordinates of said two reflection members the coordinates of said needle-line in said scan head coordinate system, and storing said cooordinates of said needle-line in said memory means.

4. The method as recited in claim 3 wherein said coordinates of said two reflection members are determined by displaying said two reflection members on said image display means, successively moving said cursor to said two reflection members on said display, determining the coordinates of said cursor at each of said two reflection members in said scan head coordinate system, and storing said cursor coordinates in said memory means.

5. The method as recited in claim 1 further comprising adjusting the spatial relationship of said needle-line relative to said scan head between at least two operative positions, determining the coordinates of the simulated needle-line for each of said at least two operative positions in said scan head coordinate systems, storing said coordinates of the simulated needle-line for each said operative position in said memory means, calculating from said stored coordinates the coordinates of said needle-line for each said operative position in said scan head coordinate system, and storing said coordinates of said needle-line for each said operative position in said memory means.

6. The method as recited in claim 1 wherein scanning of a region by said scan head is performed after immersing said mounted calibration member in a fluid.

7. A method for using an ultra-sonic imaging apparatus which includes a scan head mounted in a housing and operable for scanning a sector and defining a scan head coordinate system, memory means responsive to said scan head for storing images of a region scanned by said scan head, image display means for displaying said images stored in said memory means and for displaying a manually positionable cursor, and a biopsy attachment means mounted on said housing for positioning a biopsy needle so that its needle-line lies within the region scanned by said scan head when the needle is in operative position on said housing, said method comprising the steps of: mounting a calibration member on said biopsy attachment for simulating a biopsy needle, scanning said mounted calibration member for producing a simulated needle-line on a calibration image produced by said image display means, determining the coordinates of said scanned calibration member in said scan head coordinate system, storing said coordinates of said scanned calibration member in said memory means, calculating from said stored coordinates the coordinates of said needle-line in said scan coordinate system, and storing said coordinates of said needle-line in said memory means.

8. The method as recited in claim 7 wherein the step of determining said coordinates of said scanned calibration member in said scan head coordinate system comprises the steps of displaying said scanned calibration member on said image display means, moving said cursor to at least one point on said display of said calibration member, determining the coordinates of said cursor at said at least one point in said scan head coordinate system, and storing said cursor coordinates in said memory means.

9. The method as recited in claim 7 further comprising the steps of determining the coordinates of at least one reflection member in said scan head coordinate system, storing said coordinates of said at least one reflection member in said memory means, calculating from said stored coordinates the coordinates of said needle-line in said scan head coordinate system, and storing said coordinates of said needle line in said memory means.

10. The method as recited in claim 9 wherein the step of determining said coordinates of said at least one reflection member further comprises the steps of displaying said at least one reflection member on said display means, moving said cursor to said at least one reflection member on said display, determining the coordinates of said cursor at said at least one reflection member in said scan head coordinate system, and storing said cursor coordinates in said memory means.

11. The method as recited in claim 7 further comprising the steps of adjusting the spatial relationship of said needle-line relative to said scan head between at least two operative positions, determining the coordinates of said scanned calibration member for each of said at least two operative positions in said scan head coordinate system, storing said coordinates of said scanned calibration member for each said operative position in said memory means, calculating from said stored coordinates the coordinates of said needle-line for each said operative position in said scan head coordinate system, and storing said coordinates of said needle-line for each said operative position in said memory means.

12. The method as recited in claim 7 further comprising the steps of adjusting the spatial relationship of said needle-line relative to said scan head between at least two operative positions, determining the coordinates of at least one reflection member for each of said at least two operative positions in said scan head coordinate system, storing said coordinates of said at least one reflection member for each said operative position in said memory means, calculating from said stored coordinates the coordinates of said needle-line for each said operative position in said scan head coordinate system, and storing said coordinate of said needle-line for each said operative position in said memory means.

13. The method as recited in claim 7 wherein said scanning is performed after immersing said mounted calibration member in a fluid.

14. An ultra-sonic imaging apparatus, comprising:
(a) a housing;
(b) a scan head mounted in said housing and operable to scan a sector;
(c) a biopsy attachment means mounted on said housing for positioning a biopsy needle so that its needle-line lies within the region scanned by said scan head when the needle is in operative position relative to said scan head;
(d) image display means for displaying an image of a region scanned by said scan head when the latter is operated;
(e) a calibration member removably mounted on said biopsy attachment for simulating a biopsy needle and producing a simulated needle-line on a calibration image produced by said image display means;
(f) means for determining the coordinates of said simulated needle-line in said calibration image;
(g) a memory for storing said determined coordinates of said simulated needle-line; and
(h) means responsive to said memory for generating the coordinates of said simulated needle-line for superimposing a representation of the simulated needle-line on the image displayed on said image display means when the scan head is operated.

15. The apparatus as recited in claim 14 wherein said calibration member includes at least two reflection regions, said calibration member being disposed in a predetermined geometrical relationship with respect to said housing when said calibration member is mounted on said biopsy attachment.

16. The apparatus as recited in claim 14 further comprising means for measuring the angular orientation of said needle-line relative to said housing, and wherein said calibration member includes at least one reflection region, said calibration member being disposed in a predetermined geometrical relationship with respect to said housing when said calibration member is mounted on said biopsy attachment.

17. The apparatus as recited in claims 15 or 16 wherein said calibration member is disposed in the same predetermined geometrical relationship with respect to said housing and the latter is in said operative position when said calibration member is mounted on said biopsy attachment.

18. The apparatus as recited in claim 17 wherein each said reflection region comprises a substantially spherical reflection member.

19. The apparatus as recited in claim 18 wherein said calibration member comprises a substantially straight rod which includes each said reflection member.

20. The apparatus as recited in claim 19 wherein said biopsy attachment includes needle guide means mounted on said housing for orienting said biopsy needle toward a biopsy target, said needle guide including a bushing holder, and said calibration member comprises a bushing for insertion into said bushing holder, said rod being attached to said bushing.

21. The apparatus as recited in claim 20 further comprising adjustment means for adjusting the spatial relationship of said needle-line relative to said scan head between at least two operative positions, said calibration member for determining the coordinates of said needle-line in said scan head coordinate system for each said at least two operative positions independently of determining the particular spatial relationship of said needle-line in a said operative position relative to said scan head, and further comprising memory means for storing said coordinates of said needle-line for each said operative position.

22. A calibration member for calibrating an ultrasonic imaging apparatus on which is mounted a biopsy attachment having a first housing and needle guide means, said imaging apparatus including a scan head for scanning a region that includes a biopsy needle-line defined by a biopsy needle when the latter is mounted in said needle guide means, said calibration member comprising:

(a) a second housing having at least one reflector and mounting means for mounting said imaging apparatus; and (b) said at least one reflector and mounting means being constructed and arranged to cause the at least one reflector to lie on said biopsy needle-line when said imaging apparatus is mounted on said mounting means.

23. The apparatus as recited in claim 22 wherein said second housing includes a reservoir for holding fluid for use during calibration of said operation.

24. The apparatus as recited in claim 22 wherein said mounting means comprises means for mounting said imaging apparatus including said biopsy attachment on said second housing in at least two operative positions of said biopsy needle relative to said scan head.

25. A method for using an ultra-sonic imaging apparatus which includes a scan head mounted in a housing and operable for scanning a sector and defining a scan head coordinate system, memory means for storing an image of a region scanned by said scan head, image display means for displaying images stored in said memory means and for displaying a manually positionable cursor, and a biopsy attachment means mounted on said housing for positioning a biopsy needle so that its needle-line lies within the region scanned by said scan head when the needle is in operative position on said housing, said method comprising:

(a) mounting on said biopsy attachment means a calibration member that simulates the needle-line of a biopsy needle for producing a display of said calibration member when said scan head is operated;

(b) determining the coordinates of the simulated needle-line from said display;

(c) storing a representation of said simulated needle-line in said memory means;

(d) removing said calibration member from said biopsy attachment; and (e) operating said scan head so that a representation of the simulated needle-line appears on said display.

* * * * *